United States Patent
Kim et al.

(10) Patent No.: US 8,653,146 B2
(45) Date of Patent: Feb. 18, 2014

(54) METHOD FOR TREATING TH17 INFLAMMATORY DISEASE THROUGH INHIBITION OF VASCULAR ENDOTHELIAL GROWTH FACTOR RECEPTORS AND PHARMACEUTICAL COMPOSITION THEREFOR

(75) Inventors: Yoon Keun Kim, Pohang-si (KR); Yong Song Gho, Pohang-si (KR); Yu Sun Kim, Pohang-si (KR)

(73) Assignee: Postech Academy-Industry Foundation, Pohang-Si, Gyeongsangbuk-Do (KR)

( * ) Notice: Subject to any disclaimer, the term of this patent is extended or adjusted under 35 U.S.C. 154(b) by 0 days.

(21) Appl. No.: 13/393,479

(22) PCT Filed: May 20, 2010

(86) PCT No.: PCT/KR2010/003182
§ 371 (c)(1),
(2), (4) Date: Feb. 29, 2012

(87) PCT Pub. No.: WO2011/025128
PCT Pub. Date: Mar. 3, 2011

(65) Prior Publication Data
US 2012/0156213 A1 Jun. 21, 2012

(30) Foreign Application Priority Data
Aug. 31, 2009 (KR) .................. 10-2009-0080922

(51) Int. Cl.
*A61K 31/404* (2006.01)
*A61K 9/72* (2006.01)

(52) U.S. Cl.
USPC ......................................... 514/740

(58) Field of Classification Search
None
See application file for complete search history.

(56) References Cited

U.S. PATENT DOCUMENTS

2008/0172751 A1  7/2008  Kim et al.

FOREIGN PATENT DOCUMENTS

| JP | 2007537245 | A  | 12/2007 |
|----|-----------|----|---------|
| WO | 01/17995  | A1 | 3/2001  |
| WO | 02/41882  | A2 | 5/2002  |
| WO | 2007/009071 | A2 | 1/2007 |

OTHER PUBLICATIONS

Jost et al., Metabolism and disposition of vatalanib (PTK787/ZK-222584) in cancer patients, Drug Met. Dispos. 34(11):1817-1828, Nov. 2006.*
Drygin et al., Protein kinase CK2 modulates IL-6 expression in inflammatory breast cancer, Biochem. Biophys. Res. Comm. 415:163-167, 2011.*
Overmoyer B, Robertson K, Persons M et al. A phase I pharmacokinetic and pharmacodynamic study of SU5416 and adriamycin in inflammatory breast cancer. Breast Cancer Res Treat 2001; 69: 284, abst #432.*
Luzina et al., Roles of T lympocytes in plumonary fibrosis, J. Leukoc. Biol. 83:237-44, 2008.*
Romagnani, S., Human Th17 cells, Arthritis Res. Ther. 10:206, Apr. 18, 2008.*
Choi et al., A viral PAMP double-stranded RNA induces allergen-specific Th17 cell response in the airways which is dependent on VEGF and IL-6, Allergy, 65(10):1322-1330, Oct. 2010.*
Ellis et al., Vacular endothelial growth factor in human colon cancer: Biology and therapeutic implications, The Oncologist, 5:11-15, 2000.*
Tosolini et al., Clinical impact of different classes of infiltrating T cytotoxic and helper cells (Th1, Th2, Treg, Th17) in patients with colorectal cancer, Canc. Res. 71:1263-1271, 2011.*
Kim et al., Vascular endothelial growth factor is a key mediator in the development of T cell priming and its polarization to Type 1 and Type 17 helper cells in the airway, J. Immunol. 183:5113-5120, 2009.*
Shaheen, et al., "Effects of an antibody to vascular endothelial growth factor receptor-2 on survival, tumor vascularity, and apoptosis in a murine model of colon carcinomatosis", International Journal of Oncology, Lychnia, GR, vol. 18, No. 2, Feb. 1, 2001, pp. 221-226, XP009119033.
Iwanami, et al., "Crucial role of the interleukin-6jinterleukin-17 cytokine axis in the induction of arthritis by glucose-6-phosphate isomerase", Arthritis & Rheumatism, vol. 58, No. 3, Mar. 2008, pp. 754-763, XP009166828.
Mamluk, et al., "Preclinical development of a potent VEGFR-2 antagonist based on a novel protein scaffold (AdNectin)", American Association for Cancer Research. Proceedings of the Annual Meeting, American Association for Cancer Research, US, vol. 46, Apr. 1, 2005, pp. 714-715, XP009166865.
Tuder, et al., "Vascular endothelial growth factor of the lung: friend or foe", Current Opinion in Pharmacology, Elsevier Science Publishers, vol. 8, No. 3, Jun. 1, 2008, pp. 255-260, XP022711864, [retrieved on May 28, 2008].
Reicher, et al., "Anti-angiogenic effects and regression of localized murine AML produced by anti-VEGF and anti-Flk-I antibodies", European Journal of Haematology, vol. 75, No. 1, Jul. 2005, pp. 41-46, XP009166830.
Yuksel, et al., "Increased expression of tissue vascular endothelial growth factor and foetal liver kinase-1 receptor in seasonal allergic rhinitis and relevance to asthma component", Clinical Ano Experimental Allergy, vol. 37, No. 8, Aug. 2007, pp. 1183-1188, XP009166831.
European Search Report dated Feb. 15, 2013 of the corresponding European Patent Application No. 10812143.5.

(Continued)

*Primary Examiner* — Claire Kaufman
(74) *Attorney, Agent, or Firm* — Knobbe, Martens, Olson & Bear, LLP

(57) ABSTRACT

The present application relates to a method for treating or preventing Th17 inflammatory disease mediated with IL-6 or IL-17 by administration of medication which inhibits vascular endothelial growth factor receptors, and a pharmaceutical composition therefor.

2 Claims, 14 Drawing Sheets

(56) References Cited

OTHER PUBLICATIONS

Xue-Mei Ou et al., "VEGFR-2 antagonist SU5416 attenuates bleomycin-induced pulmonary fibrosis in mice", International Immunopharmacology, Jan. 2009, vol. 9, No. 1, pp. 70-79.

Robinson DS, Hamid Q, Ying S, Tsicopoulos A, Barkans J, Bentley AM, Corrigan C, Durham SR, Kay AB., "Predominant Th2-like bronchoalveolar T-lymphocyte population in atopic asthma", N Engl J Med 1992;326:298-304.

Grunig G, Warnock M, Wakil AE, Venkayya R, Brombacher F, Rennick DM, Sheppard D, Mohrs M, Donaldson DD, Locksley RM, et al., "Requirement for IL-13 independently of IL-4 in experimental asthma", Science 1998;282:2261-2263.

Wills-Karp M, Luyimbazi J, Xu X, Schofield B, Neben TY, Karp CL, Donaldson DD., "Interleukin-13: central mediator of allergic asthma", Science 1998;282:2258-2261.

Douwes J, Gibson P, Pekkanen J, Pearce N., "Non-eosinophilic asthma: importance and possible mechanisms", Thorax. 2002;57:643-8.

Fahy JV., "Eosinophilic and neutrophilic inflammation in asthma: insights from clinical studies", Proc Am Thrac Soc. 2009;6:256-9.

Berry M, Morgan A, Shaw DE, Parker D, Green R, Brightling C, Bradding P, Wardlaw AJ, Pavord ID., "Pathological features and inhaled corticosteroid response of eosinophilic and non-eosinophilic asthma", Thorax. 2007;62(12):1043-9.

Langrish CL, Chen Y, Blumenschein WM, Mattson J, Basham B, Sedgwick JD, McClanahan T, Kastelein RA, Cua DJ., "IL-23 drives a pathogenic T cell population that induces autoimmune inflammation", J Exp Med 2005; 201:233-240.

Curtis MM, Way SS, Wilson CB., "IL-23 promotes the production of IL17 by antigen-specific CD8 T cells in the absence of IL-12 and type-I interferons", J Immunol 2009;1:318-7.

Ciric B, El-Behi M, Cabrera R, Zhang GX, Rostami A., "IL-23 drives pathogenic IL-17 -producing CD8+ T cells", J Immunol 2009;182:5296-305.

Wu et al., "A human colonic commensal promotes colon tumorigenesis via activation of T helper type 17 T cell responses", Nat Med. 5(9):1016-22 (2009).

Lee CG, Link H, Baluk P, Homer RJ, Chapoval S, Bhandari V, Kang MJ, Cohn L, Kim YK, Mcdonald DM, Elias Ja, "Vascular endothelial growth factor (VEGF) induces remodeling and enhances TH2-mediated sensitization and inflammation in the lung", Nat Med 2004; 10:1095-1103.

Park SY, Seo EH, Song HS, Jung SY, Lee YK, Yi KY, Yoo SE, Kim YJ., "KR-31831, benzopyran derivative, inhibits VEGF-indueed angiogenesis of HUVECs through suppressing KDR expression", Int J Oneol. 2008;32:1311-5.

Brekken, et al., "Selective inhibition of vascular endothelial growth factor (VEGF) receptor 2 (KDR/Flk-1) activity by a monoclonal anti-VEGF antibody blocks tumor growth in mice", Cancer Research, Sep. 15, 2000, vol. 60, pp. 5117-5124.

Dineen, et al., "The Adnectin CT-322 is a novel VEGF receptor 2 inhibitor that decreases tumor burden in an orthotopic mouse model of pancreatic cancer", Bio Med Central Cancer, Nov. 27, 2008, vol. 8 in 9 pages.

You-Sun Kim, et al., "The role of VEGF and its receptors on airway allergic sensitization and pathogenesis of asthma", World Allergy Organization, Nov. 2007, S67-S68.

* cited by examiner

METHOD FOR TREATING TH17 INFLAMMATORY DISEASE THROUGH INHIBITION OF VASCULAR ENDOTHELIAL GROWTH FACTOR RECEPTORS AND PHARMACEUTICAL COMPOSITION THEREFOR

TECHNICAL FIELD

The present invention relates to a method for the treatment or prevention of Th17 inflammatory diseases characterized by non-eosinophilic or neutrophilic inflammation, and the pharmaceutical composition therefor.

BACKGROUND ART

It is very important to repress inflammation in the therapy of respiratory inflammatory diseases such as asthma, chronic obstructive pulmonary disease (COPD) and the like.

Asthma is a chronic inflammatory disease of the airways resulting from the hyper-response of the immune system. In the late 1980s, it was discovered that proliferating helper T cells, which develop into effector T cells, differentiate into two major subtypes of cells known as $T_h1$ and $T_h2$ cells that act to activate cellular immune and humoral immune systems, respectively, and that Th1 and Th2 cells antagonize each other. Hence, asthma is now understood as a kind of inflammation which is predominantly driven by eosinophils that are elicited by Th2 cytokines stimulated by IgE in response to an allergen [Robinson D S, Hamid Q, Ying S, Tsicopoulos A, Barkans J, Bentley A M, Corrigan C, Durham S R, Kay A B. Predominant Th2-like bronchoalveolar T-lymphocyte population in atopic asthma. N Engl J Med 1992; 326:298-304]. The Th2 cytokine IL-13 was identified to induce all the features of allergic asthma in mouse models [Grunig G, Warnock M, Wakil A E, Venkayya R, Brombacher F, Rennick D M, Sheppard D, Mohrs M, Donaldson D D, Locksley R M, et al. Requirement for IL-13 independently of IL-4 in experimental asthma. Science 1998; 282: 2261-2263; Wills-Karp M, Luyimbazi J, Xu X, Schofield B, Neben T Y, Karp C L, Donaldson D D. Interleukin-13: central mediator of allergic asthma. Science 1998; 282:2258-2261].

However, non-eosinophilic asthma, which accounts for a significant number of the cases of asthma, cannot be explained by the Th2-driven mechanism [Douwes J, Gibson P, Pekkanen J, Pearce N. Non-eosinophilic asthma: importance and possible mechanisms. Thorax. 2002; 57:643-8; Fahy J V. Eosinophilic and neutrophilic inflammation in asthma: insights from clinical studies. Proc Am Thorac Soc. 2009; 6:256-9]. In non-eosinophilic or neutrophilic asthma, neutrophils are much more predominant than eosinophils as is implied by the name. Patients with non-eosinophilic asthma have been noted to have severer asthma or suffer a higher exacerbation although there is no increase in the eosinophil population in the airways compared to patients with eosinophilic asthma. A clinical study by inhalation of corticosteroids and placebos showed that non-eosinophilic asthma was distinctly different from eosinophilic asthma and showed little response to steroid treatment [Berry M, Morgan A, Shaw D E, Parker D, Green R, Brightling C, Bradding P, Wardlaw A J, Pavord I D. Pathological features and inhaled corticosteroid response of eosinophilic and non-eosinophilic asthma. Thorax. 2007; 62(12):1043-9].

Recently, Th17 cells were discovered as a new subset of T helper cells, which are considered developmentally distinct from Th1 and Th2 cells. CD4+ or CD8+ T cells are known to produce IL-17 [Langrish C L, Chen Y, Blumenschein W M, Mattson J, Basham B, Sedgwick J D, McClanahan T, Kastelein R A, Cua D J. IL-23 drives a pathogenic T cell population that induces autoimmune inflammation. J Exp Med 2005; 201:233-240; Curtis M M, Way S S, Wilson C B. IL-23 promotes the production of IL-17 by antigen-specific CD8 T cells in the absence of IL-12 and type-I interferons. J Immunol 2009; 1:381-7; Ciric B, El-behi M, Cabrera R, Zhang G X, Rostami A. IL-23 drives pathogenic IL-17-producing CD8+ T cells. J Immunol 2009; 182:5296-305]. Although there is an expectation that Th17 cells might be associated with eosinophilic inflammation, the implication of Th17 cells or their cytokine IL-17 in asthma has not been revealed [Mo, Ji Hoon. T cell differentiation and Th17. Korean Journal of Otorhinolaryngology—Head and Neck Surgery 2008; 51:688-93]. More interestingly, continued Th17-mediated inflammatory response has recently been reported to induce the onset of colon cancer in the mucosal membrane [Wu et al. A human colonic commensal promotes colon tumorigenesis via activation of T helper type 17 T cell responses. Nat Med. 5(9):1016-22 (2009)].

In the meanwhile, overexpressed vascular endothelial growth factor (VEGF) causes airway remodeling and Th2 cells, together with endothelial cells, secrete VEGF upon allergic inflammation [Lee C G, Link H, Baluk P, Homer R J, Chapoval S, Bhandari V, Kang M J, Cohn L, Kim Y K, McDonald D M, Elias J A. Vascular endothelial growth factor (VEGF) induces remodeling and enhances TH2-mediated sensitization and inflammation in the lung. Nat Med 2004; 10:1095-1103]. Nowhere has the correlation between Th17 cells and VEGF or VEGFR (vascular endothelial growth factor receptor) been revealed prior to the present invention.

Among the main subtypes of VEGFRs are VEGFR-1, VEGFR-2 and VEGFR-3, which are also designated Flt-1, KDR or Flk-1, and Flt-4, respectively.

DISCLOSURE

Technical Problem

The present invention aims to reveal the correlation between Th17 cells and VEGF or VEGFR and the implication of Th17 cells in inflammatory diseases and to provide a method for the treatment and/or prevention of Th17-mediated inflammatory diseases.

Technical Solution

In order to achieve the object, the present invention provides a pharmaceutical composition for the therapy and/or prophylaxis of IL(interleukin)-6- or IL(interleukin)-17-mediated Th17 (T helper type 17) inflammatory diseases, comprising as an active ingredient a VEGFR pathway inhibitor in accordance with an aspect thereof.

In accordance with another aspect thereof, the present invention provides a method for the therapy and/or prophylaxis of IL-6- or IL-17-mediated Th17 inflammatory diseases, comprising administering the pharmaceutical composition to a subject in need thereof.

Advantageous Effects

The pharmaceutical composition comprising a VEGFR pathway inhibitor as an active ingredient in accordance with the present invention is effective in the therapy or prophylaxis of IL (interleukin)-6- or IL-17-mediated Th17 inflammatory disease, particularly, asthma or chronic obstructive pulmonary disease characterized by non-eosinophilic or neutrophilic inflammation.

In addition, the composition based on a selective inhibitor against the VEGFR-2-mediated signal pathway can selectively repress Th-17 type immune responses and can be effectively applied to the therapy of non-eosinophilic or neutrophilic inflammatory diseases.

Further, the composition is advantageous in that it has no effects on the cellular immune response of Th-1 so that it can reduce the side effects such as bacterial infection, etc.

BEST MODE

Figure 1:
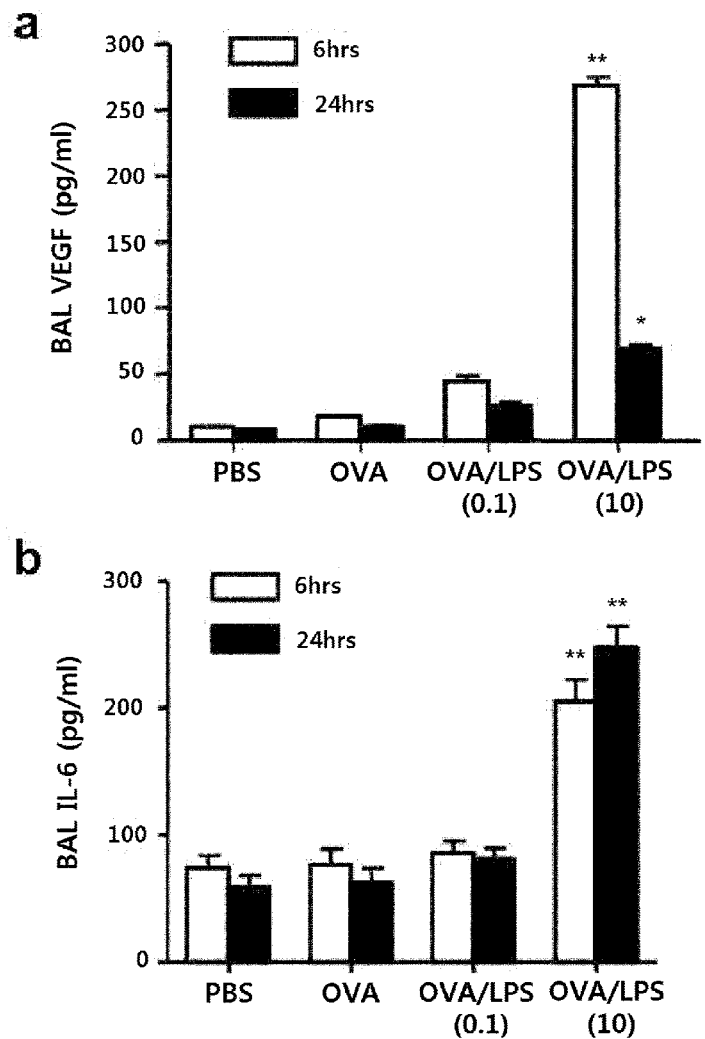
FIG. 1 shows levels of VEGF and IL-6 in the BAL fluid obtained 6 and 24 hours after intranasal sensitization with an allergen and LPS.

Reference should now be made to the drawings, to explain embodiments and examples of the present invention in detail so that those of ordinary skill in the art can easily practice them.

However, the following description is not intended to limit the present invention to specific embodiments and should be construed as including all modifications, equivalents and substituents which fall within the spirit and scope of the present invention.

In accordance with a first aspect thereof, the present invention contemplates a pharmaceutical composition for the therapy and prophylaxis of an IL-6- or IL-17-mediated Th17 inflammatory disease, comprising as an active ingredient a VEGFR pathway inhibitor.

VEGFR useful in the present invention may include VEGFR-1, VEGFR-2 and VEGFR-3 and may preferably be VEGFR-2. Hence, the VEGFR pathway inhibitor may preferably be selective for the VEGFR-2-mediated signal pathway.

In a preferred embodiment of the present invention, the Th17 inflammatory diseases include non-eosinophilic or neutrophilic asthma or chronic obstructive pulmonary disease (COPD).

In one embodiment of the present invention, the Th17 inflammatory disease may be inflammatory bowel disease, atopic dermatitis, a rheumatoid disease or an autoimmune disease, all being characterized by non-eosinophilic or neutrophilic inflammation.

In one embodiment of the present invention, the Th17 inflammatory disease may be IL-6- or IL-17-mediated colon cancer, stomach cancer or lung cancer.

As used herein, the term "VEGFR pathway inhibitor" is intended to refer to a substance which inhibits the VEGFR-mediated signal pathway by acting on the VEGFR directly or on a downstream member of the pathway, like a kinase inhibitor. Likewise, the term "VEGFR-2 pathway inhibitor," as used herein, refers to a substance which inhibits the VEGFR-2-mediated signal pathway by acting on VEGFR-2 directly or on a downstream member of the pathway, like a kinase inhibitor.

The VEGFR-2 pathway inhibitor may function to reduce Th-17-mediated immune responses or the secretion of IL-17 from Th-17 cells.

In accordance with one embodiment of the present invention, the VEGFR pathway inhibitor may be a water-soluble recombinant VEGFR protein which is inhibitory of VEGFR-2.

In one embodiment of the present invention, the VEGFR pathway inhibitor may be selected from the group consisting of semaxanib (SU5416), an anti-Flk-1 antibody, a CT-322 peptide, KR-31831, vatalanib (PTK787) and a combination thereof, and preferably the VEGFR pathway inhibitor may be selected from the group consisting of, but not limited to, an anti-Flk-1 antibody, a CT-322 peptide, KR-31831, vatalanib (PTK787) and a combination thereof, all being selectively inhibitory of the VEGFR-2 pathway.

Semaxanib, also called semaxinib or SU5416, is represented by the following Chemical Formula 1 and known to exhibit anti-tumor activity through the inhibition of angiogenesis.

[Chemical Formula 1]

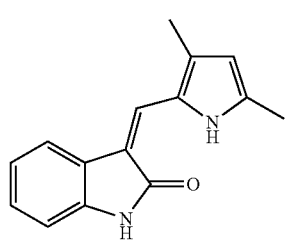

Specific for VEGFR-2 (also referred to as Flk-1), the anti-Flk-1 antibody selectively inhibits the VEGFR-2-mediated signal pathway. In accordance with one embodiment of the present invention, a variety of commercially available anti-Flk-1 antibodies (e.g., anti-mouse VEGF R2(Flk-1) antibody, R&D systems) may be employed in the present invention.

The CT-322 peptide, a small protein derived from a specific domain of human fibronectin, is known as an anti-angiogenic therapeutic agent against tumorigenesis. In one embodiment of the present invention, commercially available CT-322, such as Angiocept™ (Adnexus), may be used in the present invention.

KR-31831, represented by the following Chemical Formula, is known as an angiogenesis inhibitor with inhibitory activity against tumorigenesis by specifically inhibiting the VEGFR-2-mediated signal pathway [Park S Y, Seo E H, Song H S, Jung S Y, Lee Y K, Yi K Y, Yoo S E, Kim Y J. KR-31831, benzopyran derivative, inhibits VEGF-induced angiogenesis of HUVECs through suppressing KDR expression. Int J Oncol. 2008; 32:1311-5]:

[Chemical Formula 2]

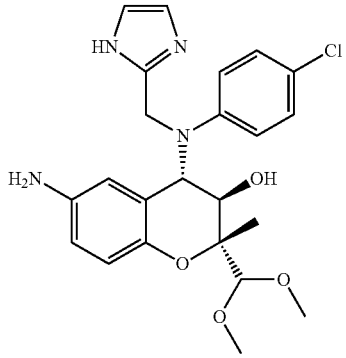

Vatalanib, also designated PTK787 or PTK/ZK, is a kinase inhibitor represented by the following Chemical Formula 3 which is highly selective for VEGFR-2 and known as an angiogenesis inhibitor against tumorigenesis.

[Chemical Formula 3]

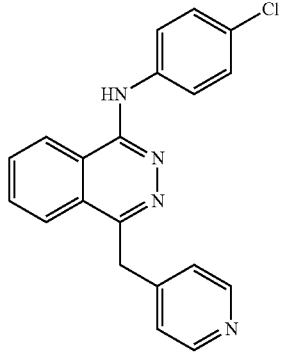

Contemplated in accordance with a second aspect of the present invention is a method for treating or preventing an IL-6- or IL-17-mediated Th17 inflammatory disease, comprising administering to a mammal in need thereof a pharmaceutical composition comprising a VEGFR pathway inhibitor as an active ingredient.

The methods of administration may be systemic administration, oral administration and inhalation through the respiratory system, but are not limited thereto. Various other administration routes may be employed.

Descriptions of the VEGFR, the VEGFR pathway inhibitor and the selective VEGFR-2 pathway inhibitor in conjunction with the pharmaceutical composition for the therapy or prophylaxis of IL-6- or IL-17-mediated Th17 inflammatory diseases in accordance with the first aspect of the present invention are true of those in the context of the method for the therapy or prophylaxis of IL-6- or IL-17-mediated Th17 inflammatory diseases in accordance with the second aspect of the present invention.

A better understanding of the present invention may be obtained through the following examples which are set forth to illustrate, but are not to be construed as limiting the present invention.

EXAMPLES

VEGFR inhibitors were assayed for inhibitory activity in asthma animal models suffering from Th17-mediated inflammation.

To construct asthma animal models, C57BL/6 (female, 6 weeks old) mice were divided into groups, each consisting of five mice and sensitized with 75 µg of ovalbumn (OVA) as an allergen and 10 µg of an endotoxin (lipopolysaccharide, LPS) as an adjuvant via an intranasal route on Day 0, 1, 2 and 7. Some mice in experiment groups were intraperitoneally injected with SU5416 (purchased from Sigma) at a dose of 1 mg/kg or 10 mg/kg, or anti-Flk-1 (purchased from R&D systems) at a dose of 0.1, 1 or 10 µg 30 min before the intranasal administration of OVA and LPS. On days 14, 15, 21 and 22, OVA (50 µg) was intranasally administered to the animals after anesthesia.

The mice were examined for pulmonary inflammation 6 hours (day 22) and 48 hours (day 24) after the last OVA administration. In this regard, the mice were anesthetized by intraperitoneal injection of a mixture of ketamin and xylazine and allowed to undergo thoracotomy to expose the trachea into which a catheter was then inserted, followed by ligation. The airway was washed by injecting 1 mL of sterile saline twice to obtain bronchoalveolar lavage (BAL) fluid. For the analysis of T lymphocytes in pulmonary tissues, cells were extracted from the local lymph nodes of the lung excised.

The BAL fluid was centrifuged at 4° C. at 3000 rpm for 10 min and the cell pellet thus formed was suspended in PBS (phosphate buffered saline). After cytospin, the cells thus collected were spread on a slide and stained with Diff Quick. In a 1000× magnified sight under an optical microscope, 300 or more inflammatory cells were observed and classified into macrophages, lymphocytes, neutrophils, and eosinophils which were then counted. In addition, levels of gamma interferon, responsible for Th1 inflammatory response, and IL-17 and IL-6, both responsible for Th17 inflammatory response, in the BAL fluid were quantified by ELISA.

The excised pulmonary tissue was treated with collagenase type IV (Sigma) to isolate cells. Their surface was stained with fluorescent-conjugated anti-CD3, CD4, and CD8 antibodies (BD Pharmingen) and holes in the cell membrane were formed with formalin, followed by intracellular cytokine staining with anti-IFN-γ and IL-17 antibodies. FACSCalibur™ (Becton Dickinson) was used to determine the kind of T cells introduced into the lung and the expression level of T cells.

The cells obtained from the lymph nodes were incubated for 72 hours in RPMI (Gibco) supplemented with 100 µg/ml OVA, 10% FBS, and an antibiotic before respective cytokines responsible for Th1-, Th17- and Th2-mediated inflammatory responses were quantified using ELISA.

FIG. 1a shows levels of VEGF in the BAL fluid obtained 6 and 24 hours after co-administration of OVA and LPS. FIG. 1b shows levels of IL-6 in the BAL fluid under the same experiment conditions. When 10 μg of LPS was administered, an increase was found in the level of VEGF in the BAL fluid within as short as 6 hours (FIG. 1a). IL-6, serving as an inflammatory index, was also detected at increased levels in the BAL fluid both 6 and 24 hours after administration of 10 μg of LPS (FIG. 1b).

For the experiment groups in which OVA had been intranasally injected after sensitization with OVA in combination with recombinant VEGF or LPS, counts were made of the inflammatory cells in the BAL fluid obtained therefrom. For control groups to which OVA was intranasally injected after sensitization with PBS or VEGF alone, counts of the inflammatory cells were also conducted. Plots of both these counts are made in FIG. 2. INF-γ and IL-17 in T cells isolated from the experiment groups (OVA/VEGF, OVA/LPS) and the control groups (PBS, VEGF) were quantitatively analyzed and the results are shown in FIGS. 3a and 3b, respectively.

Figure 2:
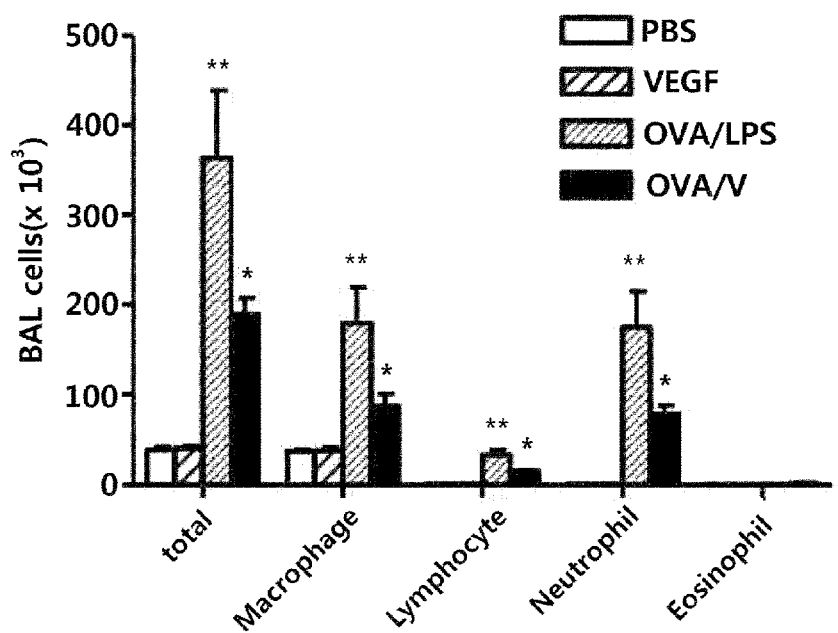
FIG. 2 shows inflammation responses in BAL fluid obtained from asthma animal models established by intranasal injection of an allergen after sensitization with an allergen in combination with an endotoxin or recombinant VEGF.
Figure 3:
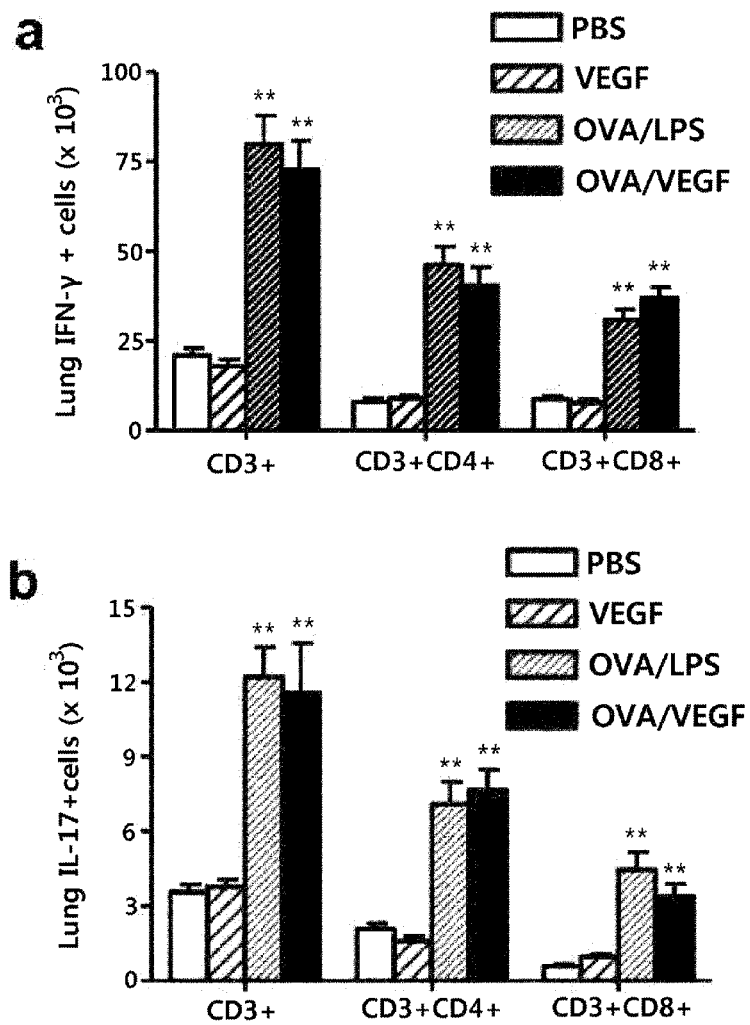
FIG. 3 shows Th1 and Th17 type immune responses in lung tissues 6 hours after the injection of an allergen into animal models sensitized with an allergen in combination with an endotoxin or recombinant VEGF.

Co-administration of recombinant VEGF and OVA (OVA/VEGF) induced an increase in the population of inflammatory cells while the population of inflammatory cells remained unchanged upon administration of VEGF alone (see FIG. 2). Likewise, the quantities of INF-γ and IL-17, both accounting for inflammation, were increased upon co-administration with VEGF and OVA whereas recombinant VEGF alone induced the secretion of neither INF-γ nor IL-17 (see FIGS. 3a and 3b).

Figure 4:
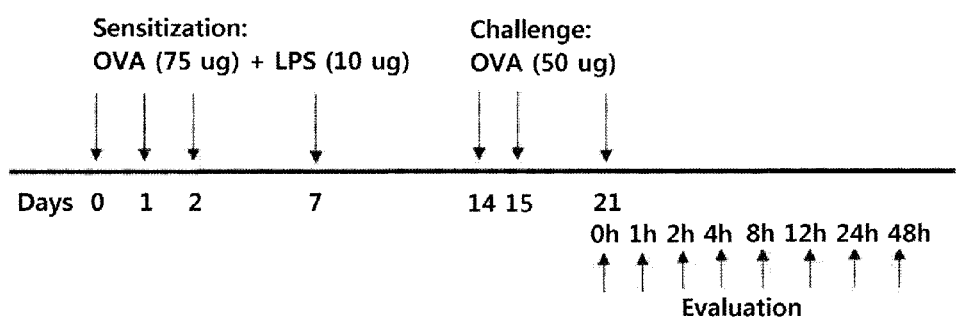
FIG. 4 is a schematic view showing the evaluation of immune responses in BAL fluid obtained from asthma animal models established by allergen challenge after sensitization with an allergen in combination with an endotoxin or VEGF according to a time schedule.

According to the protocol of FIG. 4, mice were sensitized with OVA and LPS and then administered with OVA to construct inflammatory models. On day 14, 15 and 21, the models were intranasally challenged with OVA to determine levels of inflammatory cells and IL-17 in BAL fluid vs. time as shown in FIG. 4. The results are plotted as a function of time in FIGS. 5a and 5b, respectively.

Figure 5:
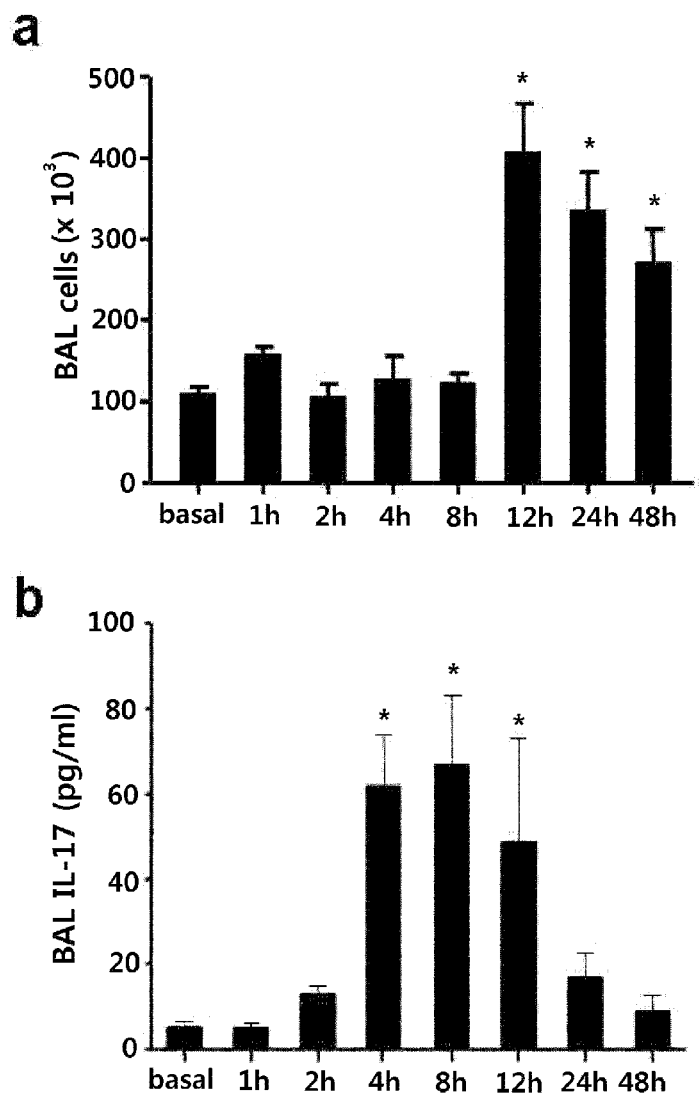
FIG. 5 shows inflammatory responses and IL-17 secretion measured in BAL fluid at the predetermined times shown in FIG. 4.

The quantity of IL-17 started to increase from 4 hours after the last challenge with OVA (see FIG. 5b). The number of inflammatory cells was increased from 12 hours after the last challenge (see FIG. 5a).

Figure 6:
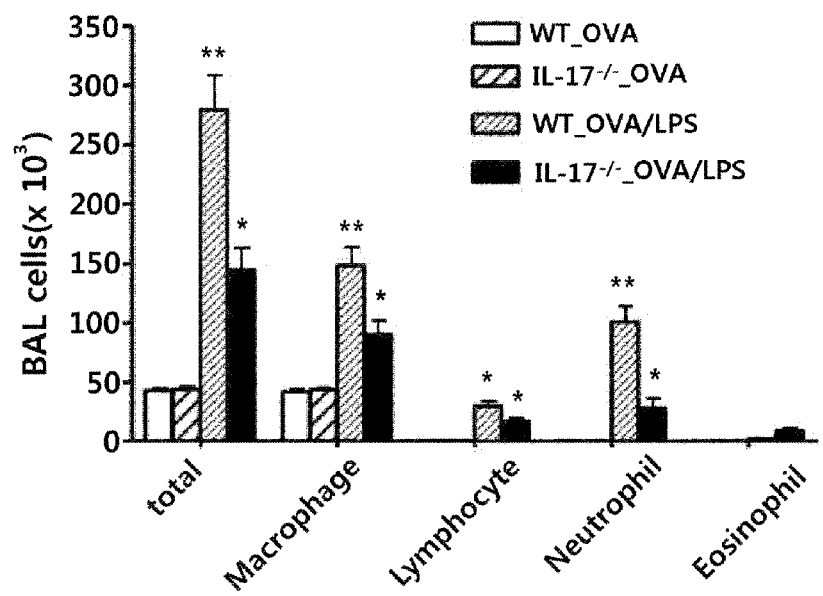
FIG. 6 shows inflammatory responses in BAL fluid from IL-17-deficient asthma animal models.

Under the same experiment condition, a much smaller population of inflammatory cells were counted in IL-17-deficient mice (IL-17$^{-/-}$_OVA/LPS) than in normal mice (WT_OVA/LPS) (see FIG. 6).

Figure 7:
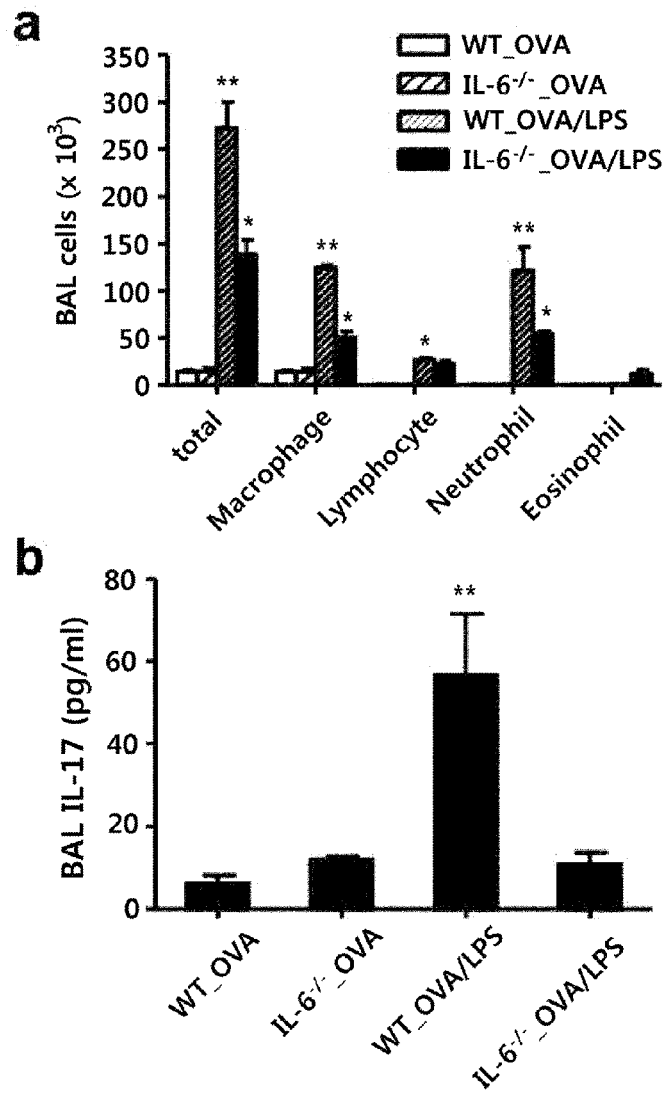
FIG. 7 shows inflammatory responses and IL-17 secretion measured in BAL fluid obtained from IL-6-deficient asthma animal models.

As for IL-6 deficient mice (IL-6$^{-/-}$_OVA/LPS), they were allowed to increase the population of inflammatory cells to a much smaller extent compared to normal mice (WT_OVA/LPS) (FIG. 7a), but with no increase in the level of IL-17 (FIG. 7b).

Example 1

Assay of SU5416 for Inhibitory Activity Against VEGFR-1 and VEGFR-2

Figure 8:
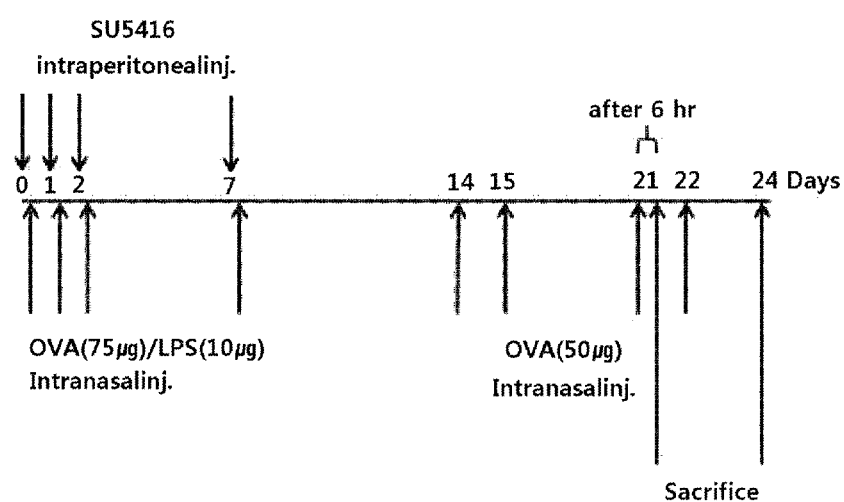
FIG. 8 shows a protocol for establishing an asthma animal model of Example 1.

C57BL/6 (female, 6 weeks old) mice were classified into experimental and control groups, each composed of 5, and established into asthma models according to the protocol of FIG. 8. Mice in the experimental groups were intraperitoneally injected with a solution of the VEGFR(-1 and -2) tyrosine kinase inhibitor SU5416 in DMSO (dimethyl sulfoxide) at a dose of 1 mg/kg or 10 mg/kg. They were intranasally sensitized with OVA and LPS starting 30 min after the intraperitoneal injection on days 0, 1, 2 and 7. Mice in the control group were intraperitoneally injected with DMSO alone and then intranasally sensitized with OVA and LPS. On days 14, 15, 21 and 22, OVA was intranasally injected into the mice under anesthesia. Inflammatory cells in BAL fluid were counted 48 hours after the last injection (day 24) and the results are shown in FIG. 9.

Figure 9:
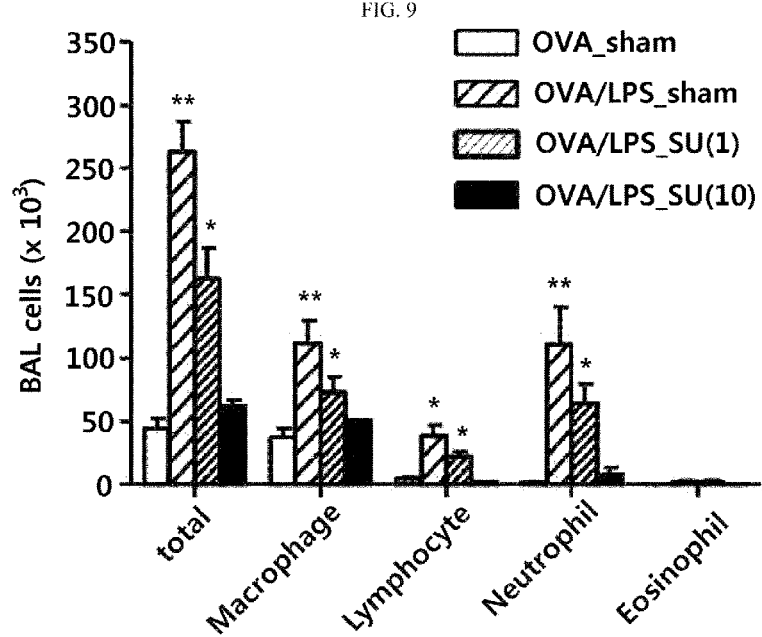
FIG. 9 shows inflammatory responses in asthma animal models treated with SU5416 almost simultaneously with the sensitization.

As can be seen in FIG. 9, the inflammatory cell count in mice, in which all signal pathways through vascular endothelial growth factor receptors had been blocked by sensitization with SU5416, was reduced in a dose-dependent manner.

Figure 10:
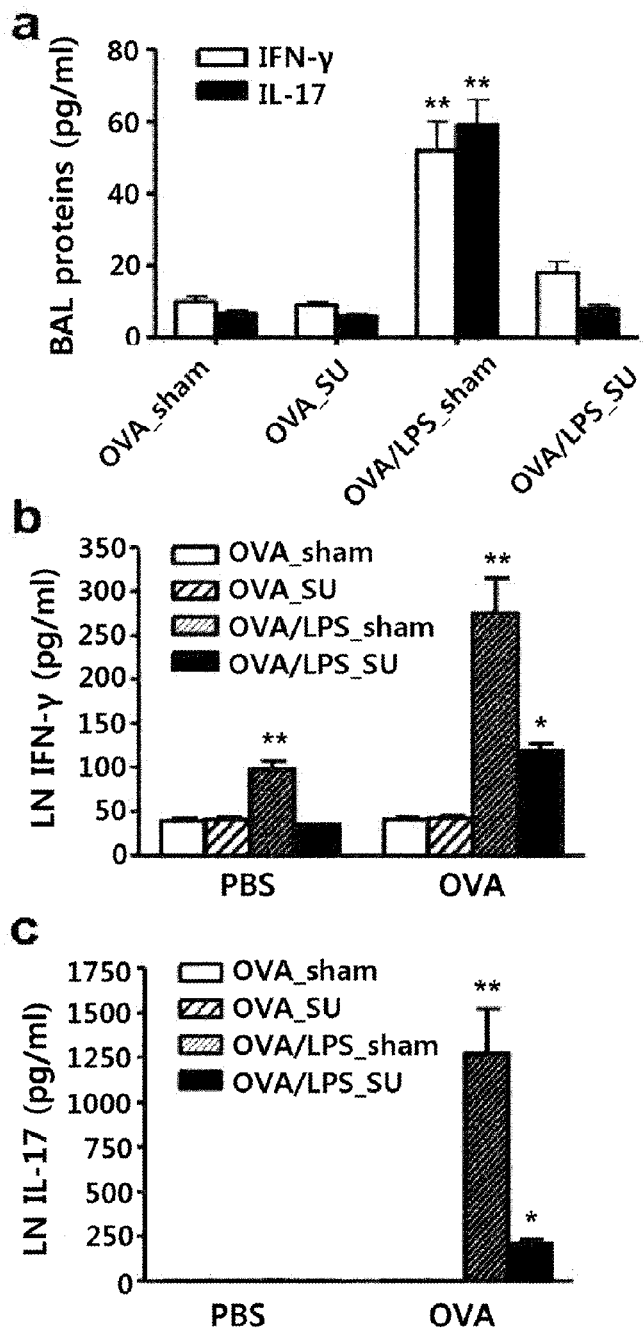
FIG. 10 shows the secretion of gamma interferon and IL-17 in the BAL fluid and the Th17 type immune responses in local lymph nodes, obtained 6 hours after allergen challenges to animal models treated with SU5416 almost simultaneously with sensitization.

FIG. 10 shows immune responses six hours after the three rounds of post-sensitization OVA challenge (day 21). The levels of both gamma interferon and IL-17 in the BAL fluid retrieved from the mice treated with SU5416 upon sensitization (OVA/LPS_SU) were observed to significantly decrease (see FIG. 10a). Immune cells isolated from local lymph nodes also had a significantly decreased level of gamma interferon and IL-17, which was secreted in response to allergen stimulus (FIGS. 10b and 10c).

Figure 11:
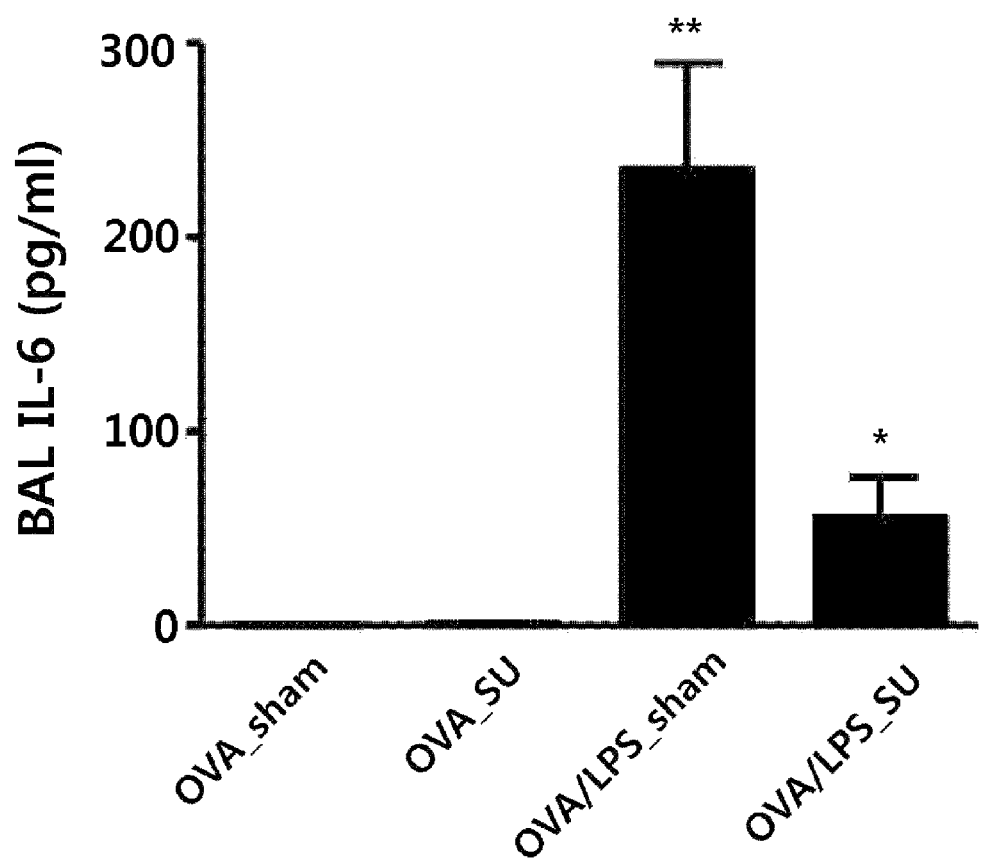
FIG. 11 shows the secretion of IL-6 in the BAL fluid from animal models treated with SU5416 almost simultaneously with sensitization.

In addition, IL-6 levels in BAL fluid obtained 6 hours after the three rounds of sensitization with OVA and LPS are shown in FIG. 11. The mice administered at a dose of 10 mg/kg with SU5416 (OVA/LPS_SU) were observed to secrete lower amounts of IL-6 than did the control (OVA/LPS_sham) (see FIG. 11).

Example 2

Assay of Monoclonal Antibody for Inhibitory Activity Against VEGFR-2

Figure 12:
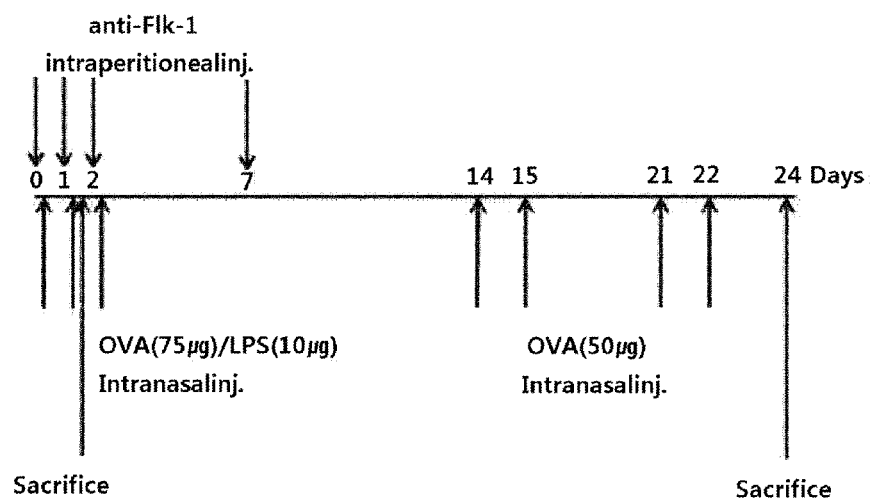
FIG. 12 is a schematic view showing a protocol for establishing an asthma animal model of Example 2.

C57BL/6 (female, 6 weeks old) mice were classified into experimental and control groups, each composed of 5, and established into asthma models according to the protocol of FIG. 12.

Figure 13:
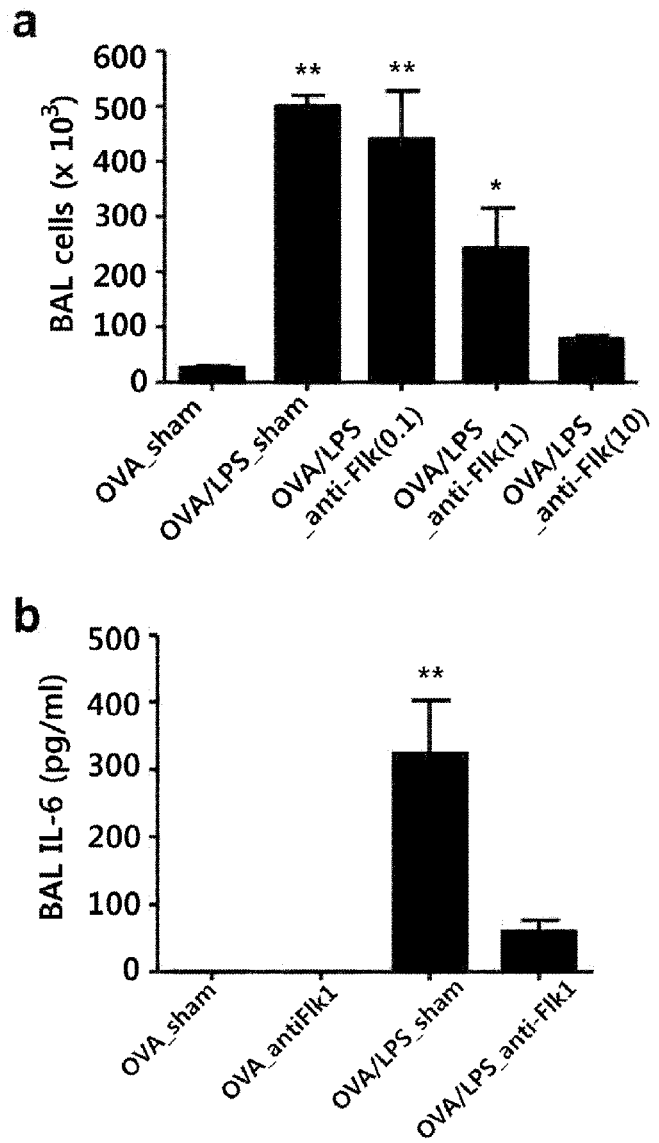
FIG. 13 shows inflammatory responses and IL-6 secretion in the BAL fluid obtained from animal models treated with anti-Flk-1 almost simultaneously with the sensitization.

Mice in the experimental groups were intraperitoneally injected with 0.1, 1.0 and 10 μg of a monoclonal antibody against VEGFR-2 (anti-Flk-1, R&D Systems) while mice in the control group were intraperitoneally injected with PBS. They were intranasally sensitized with OVA and LPS 30 min after the intraperitoneal injection of anti-Flk-1 or PBS. BAL fluid obtained 24 hours after the sensitization (day 1) was quantitatively analyzed for inflammatory cell and IL-6 levels and the results are shown in FIG. 13.

The population of inflammatory cells in the BAL fluid had decreased in an anti-Flk-1 concentration-dependent manner (see FIG. 13a). The intraperitoneal injection of 10 μg of anti-Flk-1 (OVA/LPS_anti-Flk-1) reduced the level of IL-6 in BAL fluid, compared to the sham injection to the control group (OVA/LPS_sham) (see FIG. 13b).

Figure 14:
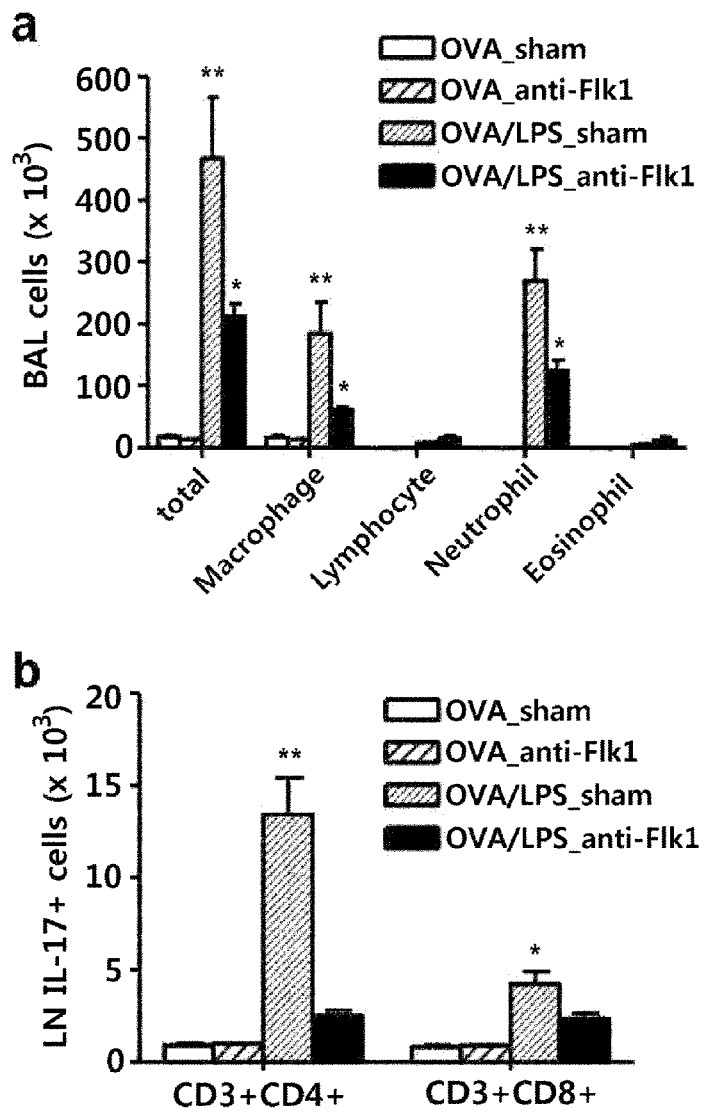
FIG. 14 shows the secretion of gamma interferon and IL-17 in the BAL fluid and the Th17 type immune responses in local lymph nodes, obtained 6 hours after allergen challenges to animal models treated with anti-Flk-1 almost simultaneously with sensitization.

Separately, mice in the experimental groups were intraperitoneally injected with 10 μg of anti-Flk-1 while mice in the control group were sham injected on days 0, 1, 2 and 7. They were intranasally sensitized with OVA and LPS 30 min after the intraperitoneal injection of anti-Flk-1 or a sham. On days 14, 15, 21 and 22, OVA was intranasally injected into the mice. Their lung inflammation and immune responses were evaluated 48 hours after the four OVA challenges and the results are shown in FIG. 14.

Compared to sham-administered mice (OVA/LPS_sham), the population of inflammatory cells in the BAL fluid of the mice treated with Anti-Flk-1 (OVA/LPS_anti-Flk-1) was significantly reduced (see FIG. 14a), and the population of IL-17 secreting CD4+ and CD8+ cells in T cells of local lymph nodes was also decreased (see FIG. 14b).

Taken together, the data obtained above demonstrate that both the non-specific VEGFR inhibitor SU5416 and the VEGFR-2 inhibitor anti-Flk-1 monoclonal antibody can excellently suppress inflammation in the lung.

From an immunological perspective, SU5416 is suppressive of Th1- and Th17-mediated immune responses while anti-Flk-1 represses Th17-mediated immune responses only. Because Th1 is responsible for cellular immunity, the long-term administration of a drug suppressive of both Th1 and Th17-mediated immune responses would result in vulnerability to bacterial infection. The selective inhibition of anti-Flk-1 against VEGFR-2 is advantageous in that only chronic Th17 type inflammatory responses can be reduced while Th1-mediated immune responses to bacterial infection are retained. Thus, it is preferred that VEGFR-2 be selectively inhibited in order to cure non-eosinophilic or neutrophilic respiratory inflammation.

Although the Examples were explained using only SU5416 and anti-Flk-1, it should be understood that other inhibitory substances which act on VEGFR or VEGFR-2 directly or on downstream members of the VEGFR or VEGFR-2 signal pathways like kinase inhibitors can be used for the purpose of the present invention. In addition to anti-Flk-1 monoclonal body, CT-322, which is derived from a domain of fibronectin, is known as a selective VEGFR-2 inhibitor. Also, KR-31831 is among selective VEGFR-2 inhibitors. Vatalanib, and a kinase inhibitor known as PTK787 or PTK/ZK, which show excellent selectivity for VEGFR-2 although acting on all types of VEGFR, can be employed in the present invention.

Moreover, various physiologically active substances including aptamers, siRNAs, and miRNAs, may be developed as having selective inhibitory activity against VEGFR-2 and used in the present invention.

VEGFR or VEGFR-2 inhibitors, although described for systemic administration, may be administered via other routes such as orally or by inhalation or by dermal application.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

INDUSTRIAL APPLICABILITY

As described hitherto, the pharmaceutical composition comprising a VEGFR pathway inhibitor as an active ingredient in accordance with the present invention is effective in the therapy of IL-6- or IL-17-mediated Th17 inflammatory disease. Particularly, the composition based on a selective inhibitor against the VEGFR-2-mediated signal pathway can be effectively applied to the therapy of non-eosinophilic or neutrophilic inflammatory diseases.

The invention claimed is:

1. A method for treating noneosinophilic or neutrophilic asthma caused by infection in a mammal, comprising administering to said mammal in need thereof a pharmaceutical composition comprising semaxanib (SU5416) and a pharmaceutically acceptable carrier.

2. The method of claim 1, wherein the administering is conducted by systemic administration, oral administration or inhalation through a respiratory organ.

* * * * *